United States Patent
Bolduc et al.

(10) Patent No.: US 10,792,468 B2
(45) Date of Patent: Oct. 6, 2020

(54) GUIDE CATHETER WITH STEERING MECHANISMS

(71) Applicant: Medtronic Vascular, Inc., Minneapolis, MN (US)

(72) Inventors: Lee Bolduc, Redwood City, CA (US); Jimmy Jen, San Jose, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 106 days.

(21) Appl. No.: 16/219,321

(22) Filed: Dec. 13, 2018

(65) Prior Publication Data
US 2019/0111239 A1   Apr. 18, 2019

Related U.S. Application Data

(62) Division of application No. 14/962,690, filed on Dec. 8, 2015, now Pat. No. 10,188,833.

(60) Provisional application No. 62/105,800, filed on Jan. 21, 2015.

(51) Int. Cl.
*A61M 25/01* (2006.01)
(52) U.S. Cl.
CPC .... *A61M 25/0147* (2013.01); *A61M 25/0133* (2013.01); *A61M 25/0136* (2013.01)
(58) Field of Classification Search
CPC .......... A61M 25/0147; A61M 25/0133; A61M 25/0136
See application file for complete search history.

(56) References Cited

U.S. PATENT DOCUMENTS

| 8,231,639 | B2 | 7/2012 | Bolduc et al. |
| 2002/0151955 | A1 | 10/2002 | Tran et al. |
| 2005/0187613 | A1 | 8/2005 | Bolduc |
| 2006/0100640 | A1* | 5/2006 | Bolduc ............ A61M 25/0136 606/108 |
| 2007/0260223 | A1 | 11/2007 | Scheibe et al. |

(Continued)

FOREIGN PATENT DOCUMENTS

| CN | 101460104 A | 6/2009 |
| EP | 2049051 A1 | 4/2009 |

(Continued)

OTHER PUBLICATIONS

PCT/US2016/013692, The International Search Report and the Written Opinion of the International Searching Authority, dated Jun. 6, 2016.

*Primary Examiner* — Rebecca E Eisenberg
*Assistant Examiner* — John A Doubrava

(57) ABSTRACT

An endovascular guide catheter includes a guide tube and a handle. The flexible guide tube has a distal end portion configured to deflect via actuation of a pull wire. The handle is coupled to the guide tube and comprises a steering assembly configured to actuate the pull wire to deflect the distal end portion of the guide tube. The steering assembly can comprise a stationary rack, a gear, a reel, and a slider. The gear engages the rack and the reel is coupled to and configured to rotate with the gear. The pull wire is coupled to the reel such that rotation of the reel causes the pull wire to wind or unwind around the reel. The slider is adapted for translation relative to the rack. Translation of the slider translates the reel relative to the rack and rotation of the gear along the rack rotates the reel.

7 Claims, 6 Drawing Sheets

(56) References Cited

U.S. PATENT DOCUMENTS

| | | |
|---|---|---|
| 2010/0168756 A1 | 7/2010 | Dorn et al. |
| 2011/0251554 A1 | 10/2011 | Romoscanu |
| 2012/0089125 A1* | 4/2012 | Scheibe ............ A61M 25/0147 |
| | | 604/523 |
| 2014/0324015 A1 | 10/2014 | Romoscanu |
| 2016/0331932 A1* | 11/2016 | Davies .............. A61M 25/0136 |

FOREIGN PATENT DOCUMENTS

| | | |
|---|---|---|
| JP | 2002527179 A | 8/2002 |
| JP | 2009512497 A | 3/2009 |
| WO | 2007046953 A2 | 4/2007 |

\* cited by examiner

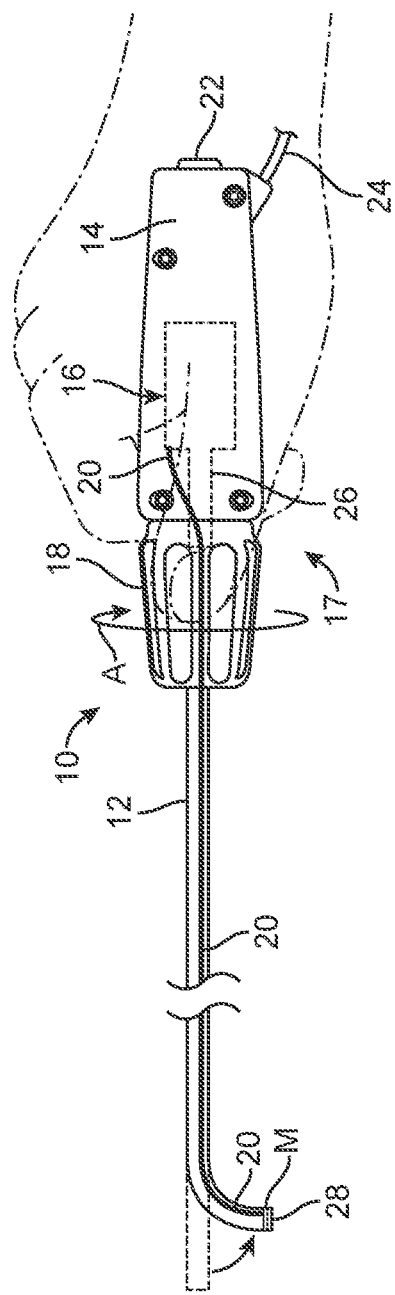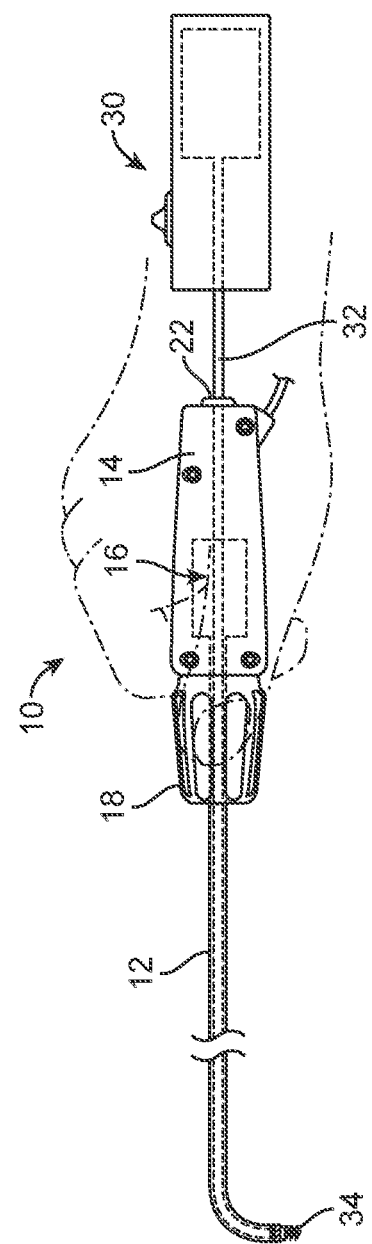

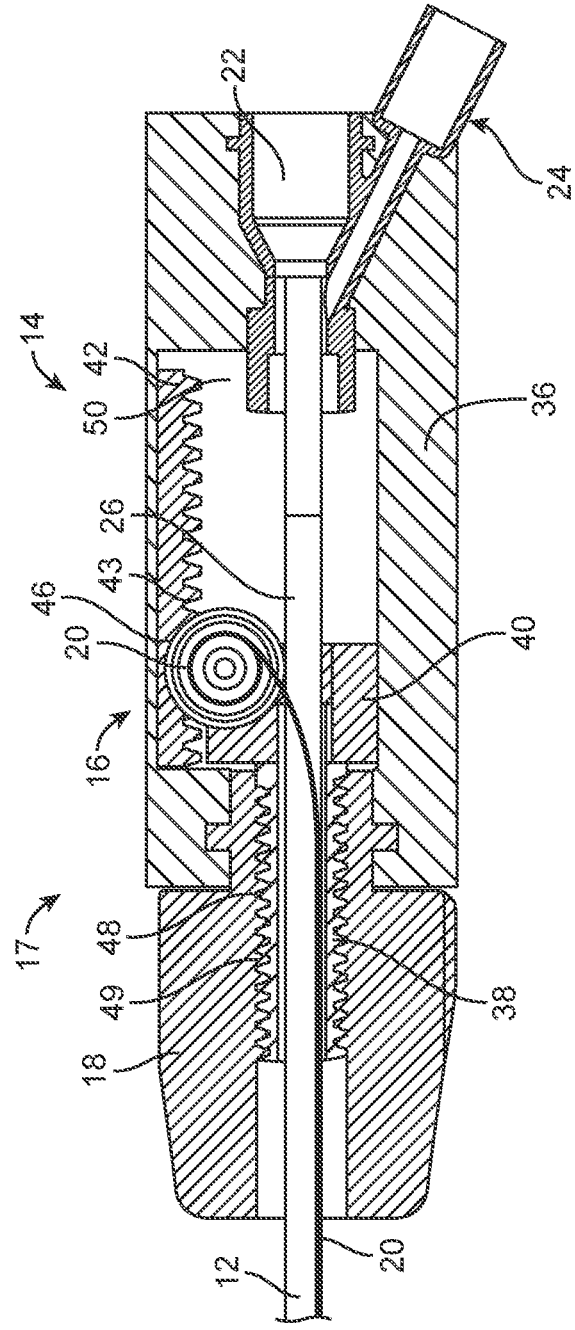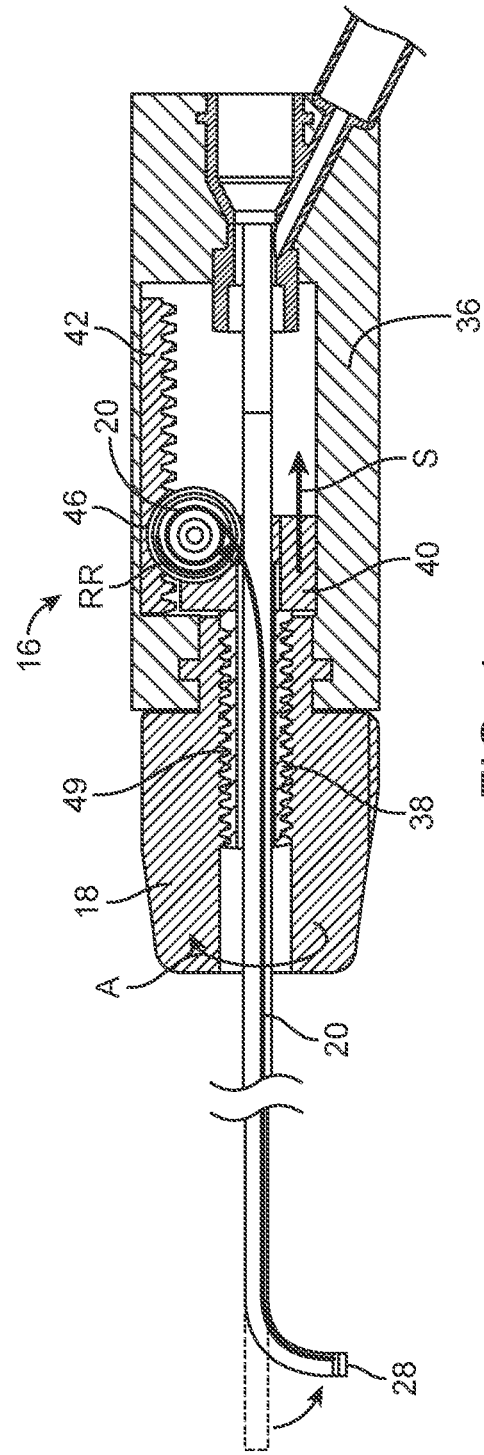
FIG. 3
FIG. 4

GUIDE CATHETER WITH STEERING MECHANISMS

RELATED APPLICATIONS

This application is a divisional of pending U.S. patent application Ser. No. 14/962,690, entitled "GUIDE CATHETER WITH STEERING MECHANISMS", filed Dec. 8, 2015, which claims the benefit of U.S. Provisional Application No. 62/105,800 filed on Jan. 21, 2015, entitled "GUIDE CATHETER WITH STEERING MECHANISMS" of Lee Bolduc et al., which is incorporated herein by reference in its entirety.

BACKGROUND

Steerable guide catheters have been developed for various procedures including endovascular. Steerable guide catheters can allow a physician to direct various types of treatment to a desired area within a patient.

SUMMARY

Embodiments according to this disclosure are directed to guide catheters, and in particular, to guide catheters having steering mechanisms that allow for deflection of a distal end portion of the catheter. Such steerable guide catheters can be used to aid in the delivery of stents, grafts, stent-grafts, balloons, wires, fasteners, etc. to various parts of the patient's anatomy including the abdominal aorta.

In some instances, current steerable guide catheters can require an undesirable amount of manipulation by a physician in order to achieve a desired deflection of a distal tip of the catheter. Additionally, some steerable guide catheters may be overbuilt (e.g., have too large a profile, have more components or more moving components than is necessary) given procedure requirements.

Thus, in one embodiment, a guide catheter is presented that has steering mechanisms that provide a sufficient mechanical advantage with a minimal amount of manipulation by the physician, and, at the same time, is packaged in an efficient and compact manner. Thus, the disclosed guide catheters can increase physician efficiency by reducing manipulation and overall procedure time. In accordance with other embodiments, guide catheters having steering mechanisms that reduce the number of catheter components, thereby reducing device complexity and cost are presented.

In one embodiment, an endovascular guide catheter is disclosed. The guide catheter includes a flexible guide tube, a pull wire, a handle and a steering assembly. The guide tube has a distal end portion configured to deflect via actuation of the pull wire. The handle is coupled to the guide tube and comprises the steering assembly. The steering assembly is configured to actuate the pull wire to deflect the distal end portion of the guide tube. According to one embodiment, the steering assembly comprises a stationary rack, a gear, a reel, and a slider. The gear engages the rack and the reel is coupled to and configured to rotate with the gear. The pull wire is coupled to the reel such that rotation of the reel causes the pull wire to wind or unwind around the reel. The slider is adapted for translation relative to the rack. Translation of the slider translates the reel relative to the rack and rotation of the gear along the rack rotates the reel.

In another embodiment, an endovascular guide catheter is disclosed. The guide catheter includes a flexible guide tube, a pull wire, a handle and a steering assembly. The guide tube has a distal end portion configured to deflect via actuation of the pull wire. The handle is coupled to the guide tube and comprises the steering assembly. The steering assembly is configured to actuate the pull wire to deflect the distal end portion of the guide tube. According to one embodiment, the steering assembly can comprise an actuator, a non-self-locking lead screw, and a slider. The actuator is configured to rotate about a longitudinal axis of the guide catheter. The actuator has a locking feature adapted to lock rotation of the actuator. The non-self-locking lead screw is coupled to the actuator for rotation therewith. The slider is coupled to the lead screw and has the pull wire attached thereto. The slider and lead screw can be coupled such that rotation of the lead screw causes translation of the slider.

The details of one or more embodiments of the disclosure are set forth in the accompanying drawings and the description below.

BRIEF DESCRIPTION OF DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

FIG. 1 is a perspective view of a steerable guide catheter illustrating a clinician's hand rotating an actuator knob to operate an associated steering assembly to cause deflection of a distal end portion of the catheter in accordance with one embodiment of this disclosure.

FIG. 2 depicts the steerable guide catheter of FIG. 1 used in combination with an operative tool in accordance with one embodiment of this disclosure.

FIG. 3 is a cross-sectional view of a steerable guide catheter including a steering assembly in accordance with one embodiment of this disclosure.

FIG. 4 depicts the steerable guide catheter of FIG. 3 being manipulated to deflect the distal end portion of the catheter in accordance with an embodiment of this disclosure.

DETAILED DESCRIPTION

Figure 5:
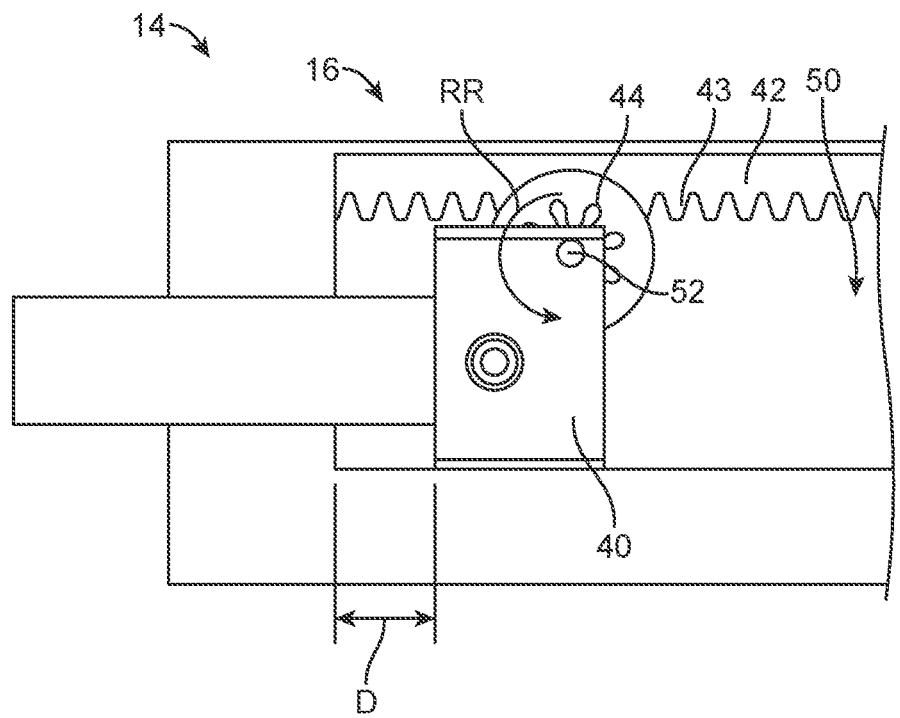
FIG. 5 is an enlarged view of a portion of a handle showing linear travel of a slider and linear and rotational travel of a gear relative to a rack of the steerable guide catheter in accordance with an embodiment of this disclosure.

This specification discloses various devices, systems, and methods related to steerable guide catheters. More particularly, the specification discloses steering assemblies that allow for deflection of a distal end portion of a guide tube of the catheter with a minimal number of components and a minimal amount of manipulation by the physician. The disclosed guide catheters can assist other operative tools in the delivery and/or implantation of various implants including stents, grafts, stent-grafts, balloons, wires, and fasteners, etc. In one embodiment, the steerable guide catheters disclosed can assist in the delivery of fasteners used to secure various prostheses and/or tissue as part of a vascular repair or other medical procedure. Embodiments according to this disclosure have application in procedures for the repair of diseased and/or damaged sections of a hollow body organ and/or blood vessel, including, e.g., repair of an aneurysmal section of the aorta.

Clinicians' desire a steerable guide catheter that allows for a comfortable amount of rotational manipulation to be translated into an effective distal catheter deflection. Such a comfortable amount of rotational manipulation can be achieved by lead screws having a fast-pitch, i.e., a lead screw having threads with a pitch greater than 5°. While the use of a fast-pitch lead screw is desirable as it allows for a comfortable amount of rotational manipulation with the use of a minimal number of components, a fast-pitch lead screw presents engineering and operational challenges. For example, fast-pitch lead screws are non-self-locking. Because fast-pitch lead screws are non-self-locking, the clinician cannot simply rotationally manipulate the steerable guide catheter to a desired position and then maintain that position without the use of the clinician's hand or another locking structure providing force to maintain positional engagement. More specifically, if a non-self-locking lead screw is used without additional locking mechanisms, the clinician would rotationally manipulate the steerable guide catheter to a desired position, e.g., a deflected distal position, release the steering mechanism actuator, and then the lead screw would travel back toward a neutral position due to the tension exerted on the lead screw by a pull wire that connects the lead screw to the distal end portion of the catheter guide tube. In part, embodiments address the engineering and operational challenges posed in using a non-self-locking lead screw.

Embodiments according to this disclosure provide a mechanical advantage sufficient to translate relatively small increments of clinician manipulation into relatively larger increments of guide tube deflection with the use of a minimal number of components. To that end, embodiments according to this disclosure provide for a steering mechanism that utilizes a compound motion, e.g., translational movement as well as rotational movement, of a reel to tension and relax a pull wire used to deflect the guide tube. Further embodiments according to this disclosure provide for the use of a fast-pitch lead screw that can be manipulated to a desired position and passively locked or otherwise maintained in that position in order to free the hands of the clinician for other tasks.

When referring to the guide catheter and/or operative tool that are manipulated by a physician or operator, the terms "proximal" and "distal" will be used to describe the relation or orientation of the apparatus or device with respect to the operator as it is used. Therefore, the term "proximal" will be used to describe a relation or orientation of the device that, when in use, is positioned toward the operator, i.e., at the handle end of the device, and the term "distal" will be used to describe a position or orientation of the device that, when in use, is positioned away from the operator, i.e., at the other end of a catheter or the like away from the handle.

FIGS. 1 and 2 show a steerable guide catheter 10 in accordance with an embodiment of the present disclosure. The steerable guide catheter 10 includes a flexible guide tube 12, a handle 14, a steering mechanism 16, an actuator 18, a pull wire 20, a proximal opening 22, an infusion valve 24 and a guide passage 26. The guide tube 12 includes a distal end portion 28 and one or more radiopaque markers M. FIG. 2 shows an operative device 30 coupled to the steerable guide catheter 10. The steerable guide catheter 10 can be used to establish an open path through which the operative device 30, sometimes called an operative tool 30, can be deployed for use as illustrated in FIG. 2.

The guide tube 12 is carried by the handle 14. In the embodiment of FIG. 1, the handle 14 is adapted to house the steering mechanism 16 therein. The actuator 18 comprises a knob and internal components that can be rotationally manipulated as indicated by arrow A. The actuator 18 is disposed at a distal end of the handle 14. The actuator 18 is coupled to the steering mechanism 16 such that together these components comprise a steering assembly 17. The pull wire 20 can comprise, for example, a Kevlar cord or control wire, and is coupled to the distal end portion 28 of the guide tube 12. The pull wire 20 travels substantially an entire length of the guide tube 12 from the distal end portion 28 to couple with the steering mechanism 16. More particularly, the pull wire 20 can travel within a lumen such as guide passage 26 or another dedicated lumen through the guide tube 12, actuator 18 and portions of the handle 14 to the steering mechanism 16.

The proximal end of the handle 14 can be provided with the proximal opening 22 and infusion valve 24. The proximal opening 22 is adapted to receive a tube 32 of the operative device 30 as illustrated in FIG. 2. The tube 32 can pass through the proximal opening 22, through a hemostatic seal assembly (not shown), guide passage 26 and guide tube 12 to the distal end portion 28. As illustrated in the embodiment of FIG. 2, the operative tool 30 can comprise a fastener applier that delivers one or more helical fasteners 34. Although illustrated in reference to a fastener applier in FIG. 2, the operative tool 30 can comprise any tool capable of delivering a desired implant. Such tools can include tools that deliver stents, balloons, wires, etc.

The flexible guide tube 12 may be constructed, for example, by extrusion using standard flexible, medical grade plastic materials. The guide tube 12, while flexible, may have a plastic memory or bias that normally orients the distal end portion 28, sometimes called the distal end region 28, of the guide tube 12 in an essentially straight configuration, as shown by the shadow lines in FIG. 1. The steering mechanism 16 can be used to enable greater control of the orientation of the distal end portion 28 even if a plastic memory or bias is used to create a bent distal region.

The handle 14 can be sized to be conveniently held by a clinician, and can be sized to introduce the guide tube 12 into an interior body region that has been targeted for treatment. The handle 14 may be constructed, for example, from molded plastic. In operation, the steering mechanism 16 is actuated by actuator 18 to deflect the distal end portion 28 of guide tube 12 out of its essentially straight configuration and into a bent or deflected configuration, as shown in FIG. 1. This is accomplished by the pull wire 20 which is coupled at or adjacent the distal end portion 28 and is tensioned by the steering mechanism 16 to provide a force that deflects the distal end portion 28. As will be discussed in further detail subsequently, the steering mechanism 16 is adapted to hold the distal end portion 28 of the guide tube 12 in its deflected condition, thereby maintaining the operative device 30 in its desired relationship during use. The steerable guide tube 12 obviates the need to equip the operative tool 30 with an on-board steering mechanism or a guide wire lumen.

As shown in FIG. 2, the guide tube 12 can be placed into its bent or deflected configuration before passage of the operative tool 30 (i.e. the tube 32) through the handle 14 and the guide tube 12. Once in a deflected configuration, the operative tool 30 can be advanced and guided by the deflection (e.g., the bent configuration) into the desired relationship with the tissue surface for use.

According to one embodiment, the operative tool 30 of FIG. 2 can comprise a powered device that applies helical fastener(s) 34. A representative embodiment of an endovascular device that, in use, applies a helical fastener is described in Bolduc et al., U.S. Pat. No. 8,231,639, issued Jul. 31, 2012, entitled "Systems and Methods for Attaching a Prosthesis Within a Body Lumen or Hollow Organ," which is incorporated herein by reference. In use, the endovascular fastener applier can be manipulated through the steerable guide catheter 10 with the distal tip deflected toward a tissue wall to apply one or more fasteners 34 to a prosthesis (not shown) that is deployed to repair diseased and/or damaged sections of a hollow body organ and/or a blood vessel, e.g., to repair an aneurysm in the aorta.

As illustrated in FIGS. 1 and 2, the steering mechanism 16 can be configured to provide a mechanical advantage sufficient to translate relatively small increments of clinician control into relatively larger increments of guide tube deflection. In use, the steerable guide catheter 10 can be introduced to the targeted tissue site through a conventional intravascular approach. For example, when the targeted tissue site is in the aorta, the guide catheter 10 can be introduced through the femoral artery. However, other access sites and methods can be utilized.

As FIGS. 1 and 2 generally show, the actuator 18 can be manipulated by the clinician and then locked or otherwise maintained in a desired position. The operative tool 30 can then be advanced (not shown). In some instances such as illustrated in FIG. 2, the actuator 18 may be further manipulated by the clinician if desired with the operative tool 30 residing in the guide catheter 10.

FIG. 3 shows a cross-sectional view of the handle 14 according to an embodiment of the present disclosure. FIG. 3 also illustrates the pull wire 20, a portion of the guide tube 12, and the guide passage 26. FIG. 3 illustrates components of the handle 14 previously discussed such as the proximal opening 22 and the infusion valve 24 (part of the hemostatic seal assembly) but also illustrates a housing 36. The steering assembly 17 comprises the steering mechanism 16 and the actuator 18. The steering mechanism 16 includes a threaded rod 38, a slider 40, a rack 42, a gear 44 (FIGS. 5 and 6), and a reel 46.

As illustrated in FIG. 3, the handle 14 generally comprises the housing 36, the steering assembly 17 and additional components. The steering mechanism 16 is coupled to the actuator 18 and together these comprise the steering assembly 17. The actuator 18 is coupled to a distal end of the handle 14 while the steering mechanism 16 is disposed within the handle 14 (within housing 36). More particularly, the actuator 18 includes an internal threaded portion 49 that is adapted to mate with threads 48 of rod 38. Thus, the rod 38 is configured for rotation and translation relative to the actuator 18. The rod 38 can contain a hollow central passage that can accommodate the guide passage 26 as well as other lumens (e.g. a dedicated lumen of the pull wire 20).

The handle 14 includes a cavity 50 that is defined by the housing 36. Components of the steering mechanism 16 are disposed within the cavity 50. The rod 38 extends into the handle 14 and is coupled at a proximal end to the slider 40. The slider 40 is retained within the handle 14 adjacent the rack 42 and is adapted for translation (but not rotation) relative to the rack 42. Like the rod 38, the slider 40 can be adapted with a passage to accommodate the guide passage 26 as well as other lumens. Additionally, the slider 40 can be adapted to at least partially receive the gear 44 (FIGS. 5 and 6) and reel 46 therein.

Figure 6:
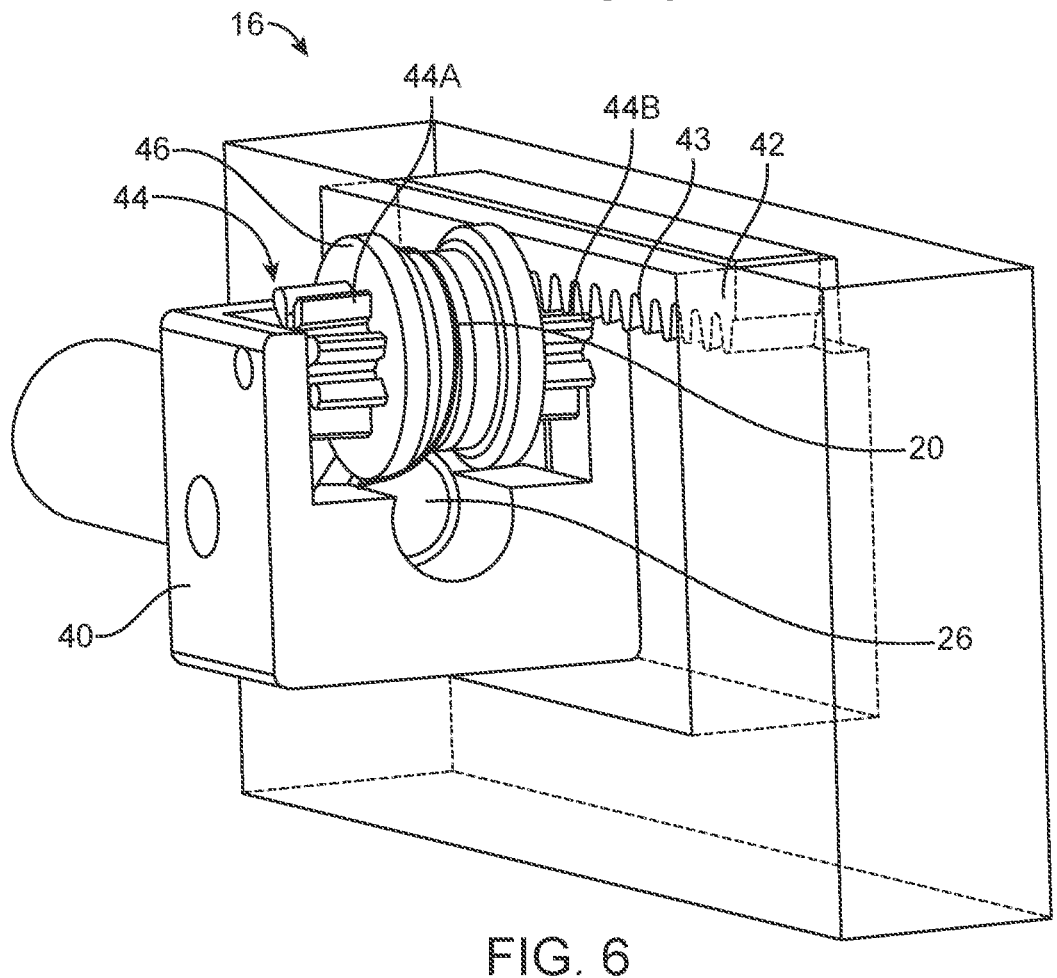
FIG. 6 is a perspective view from a proximal position showing the slider, gear, rack and reel in accordance with one embodiment of the present disclosure.

The rack 42 is disposed within the cavity 50 and is mounted to the housing 36. Thus, the rack 42 is stationary relative to other components of the steering mechanism 16 such as the slider 40, gear 44 (FIGS. 5 and 6), and reel 46. The gear 44 (FIGS. 5 and 6) is coupled to the slider 40 and is configured to engage with teeth 43 of the rack 42. The reel 46 is coupled to and configured to rotate with the gear 44 (FIGS. 5 and 6). The pull wire 20 is coupled to the reel 46 such that rotation of the reel 46 causes the pull wire 20 to wind or unwind around the reel 46.

According to some embodiments, a second rack portion (not illustrated in the cross-section) is arranged substantially parallel with the portion of the rack 42 illustrated. Thus, each rack portion is disposed generally parallel with the other to either side of the reel 46 and the gear (e.g., gear 44 of FIGS. 5 and 6) can have two gear components, each gear component is adapted to engage a corresponding one of the two rack portions.

FIG. 4 illustrates operation of the steering assembly 17 described in FIG. 3 to deflect the distal end portion 28 of the guide tube 12. As shown in FIG. 4, the steering mechanism 16 is being operated from a non-deflected position (i.e. a no pull wire tension or minimal pull wire tension position) toward another position to exert more tension on the pull wire 20, and thereby deflect the distal end portion 28. In the embodiment provided, the actuator 18 is configured to rotate about a longitudinal axis of the guide device as illustrated by arrow A to drive the translation of the threaded rod 38 and the slider 40 relative to the rack 42. More particularly, rotation by the actuator 18 (e.g., knob and internal components) translates the slider 40 in a generally proximal direction as illustrated by arrow S. Translation of the slider 40 engages the gear 44 (FIGS. 5 and 6) along the rack 42 causing rotation of the gear 44 and the reel 46 relative to the slider 40 and rack 42. Rotation of the reel 46 (indicated by the arrow RR) acts to wind the pull wire 20. Additionally, translation of the reel 46 due to translation of the slider 40 tensions the pull wire 20. Thus, a travel distance of the pull wire 20 comprises a combination of a linear travel of the reel 46 and an amount of winding or unwinding due to rotation of the reel 46.

FIG. 5 illustrates a distal portion of the handle 14 comprising the steering mechanism 16. The gear 44 is coupled to the slider 40 and is configured for rotation relative thereto. Indeed, the embodiment of FIG. 5 illustrates the gear 44 is directly coupled via only a pin 52 to the slider 40. FIG. 5 shows the slider 40 translated a distance D proximally within the cavity 50. Translation of the slider 40 engages the gear 44 along the rack 42 and causes rotation of the gear 44 (as illustrated by arrow RR).

FIG. 6 is a perspective view of the steering mechanism 16 from a proximal location. Only a portion of the pull wire 20 and the guide passage 26 is shown in FIG. 6 with the pull wire 20 passing through the guide passage 26 to couple to the reel 46. As shown in FIG. 6, the gear 44 can comprise a first gear component 44A and a second gear component 44B according to some embodiments. Each gear component 44A and 44B has teeth adapted to engage with teeth 43 of a corresponding rack 42 portion (only one rack portion is illustrated in FIG. 6). In some instances, the gear 44 and the rack 42 are adapted to be self-locking such that the reel 46 cannot wind or unwind the pull wire 20 without actuation by a user (e.g., a clinician). In the embodiment provided, the reel 46 is integral with the gear 44 such that the reel 46 is directly coupled without further intermediate components to the gear 44. Similarly, according to some embodiments, the gear 44 can be directly coupled without intermediate components to the slider 40, i.e., the gear 44 can use only the pin 52 of FIG. 5 to couple with the slider 40.

FIGS. 4 to 6 show embodiments where a ratio of the amount of rotation of the actuator 18 to an amount of rotation of the reel 46 is controlled by the pitch of the thread 48 (see FIG. 3) on the rod 38 and a number of teeth 43 on the rack 42 and the gear 44 among other factors. According to one embodiment, if two full turns comprises a number of turns of the actuator 18 deemed to be satisfactory by a clinician to achieve deflection of the distal tip of the catheter, than other design parameters (e.g., the number of teeth per gear 44, diameter of the reel 46, pitch of the gears 44 and rack 42, number of turns per inch by threads 48 on rod 38, a maximum travel along the rack 42 by the gear 44, etc.) can be selected to achieve this design goal. It has been demonstrated that two full turns of the actuator 18 can achieve a 0.65 inch travel distance by the pull wire 20. This travel distance can comprise a combination of a linear travel of the reel 46 (e.g., 0.25 inches) and an amount of winding (e.g., 0.40 inches) due to rotation of the reel 46.

Figure 7:
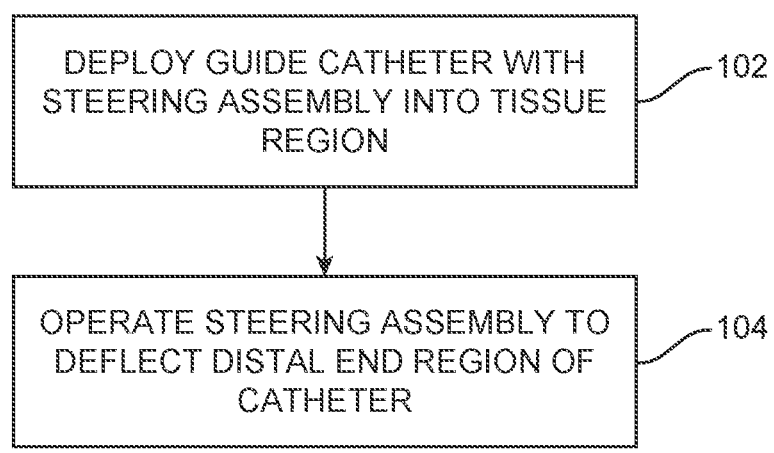
FIG. 7 shows a method in accordance with an embodiment of this disclosure.

FIG. 7 depicts a method according to an embodiment of the present disclosure. In operation 102, the method deploys a guide device (catheter) with a steering assembly comprising a rack, a reel, and a gear into an interior tissue region. The gear can engage the rack and the reel can be coupled to the gear for rotation and translation relative to the rack. In an operation 104, the method operates the steering assembly to deflect a distal end portion (region) of a guide tube coupled to the guide device. The method can include rotating the reel to wind or unwind a pull wire about the reel to apply a force to deflect the distal end portion. The force additionally comprises a tension on the pull wire due to a linear travel of the reel.

According to further embodiments of the present disclosure, the method can be used in combination with passing an operative tool configured to apply one or more fasteners to tissue through the guide device. In further embodiments, the method can operate the operative tool while residing in the guide device to apply the one or more fasteners to tissue.

The above disclosure describes an exemplary steerable guide catheter that provides a mechanical advantage sufficient to translate relatively small increments of clinician control into relatively larger increments of guide tube deflection. The exemplary steerable guide catheter additionally provides that the steerable guide catheter can be manipulated by the clinician and then locked or otherwise maintained in a desired position (e.g., a position with the distal tip of the guide tube deflected toward a wall of a vessel).

Figure 8:
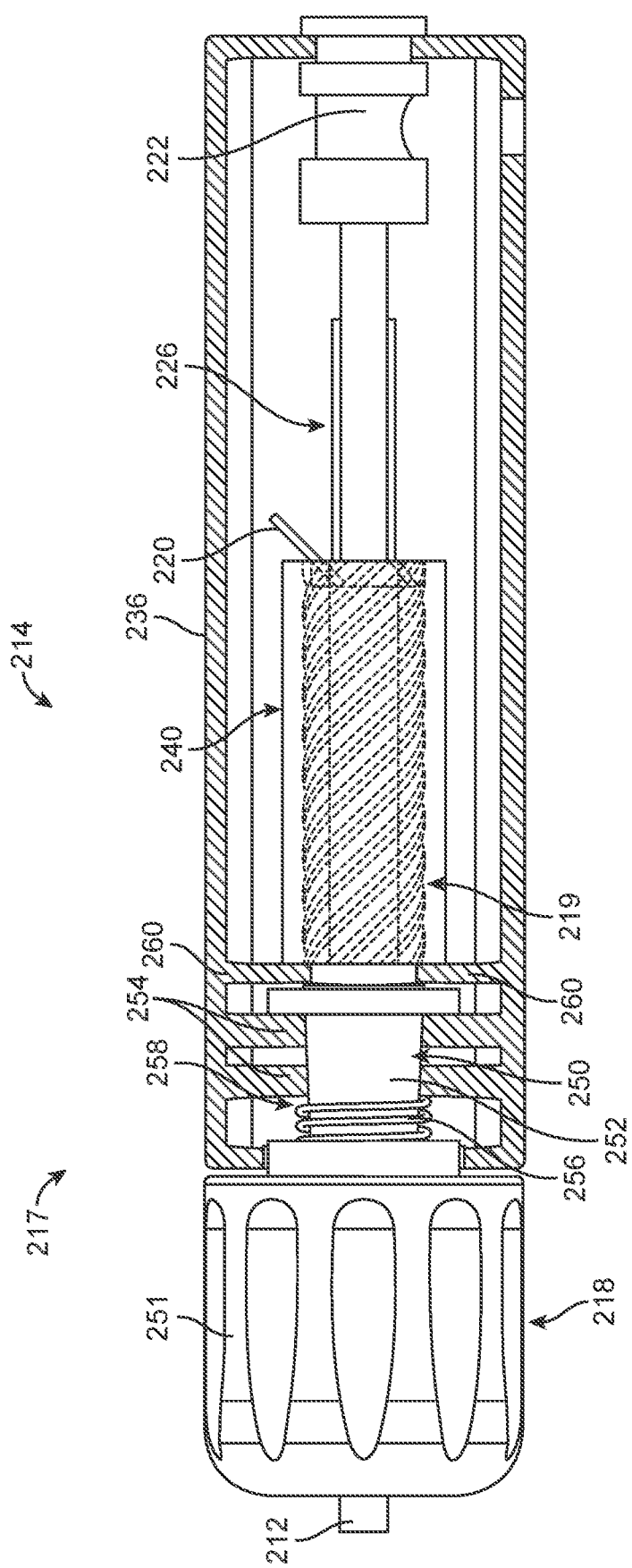
FIG. 8 depicts another handle of a steerable guide catheter including a steering assembly and locking mechanism in accordance with one embodiment of this disclosure.
Figure 9:
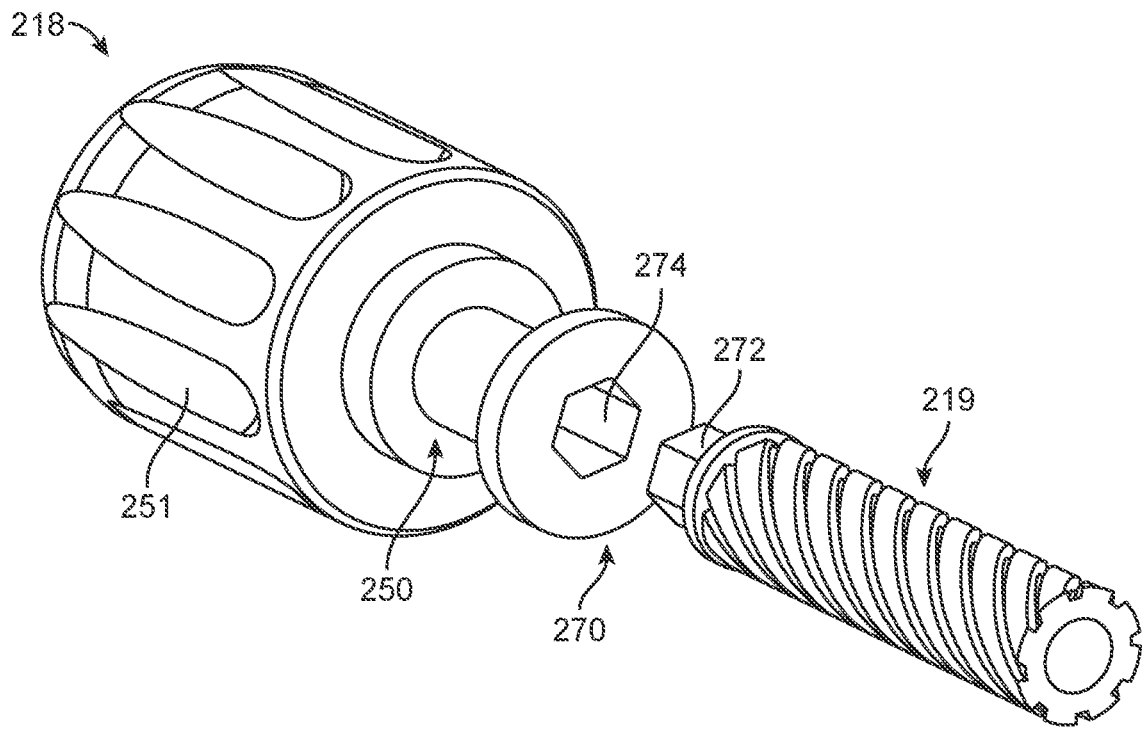
FIG. 9 is a perspective view of components of the steerable guide catheter of FIG. 8 including an actuator, taper lock, coupling feature, and lead screw in accordance with an embodiment of this disclosure.
Figure 10:
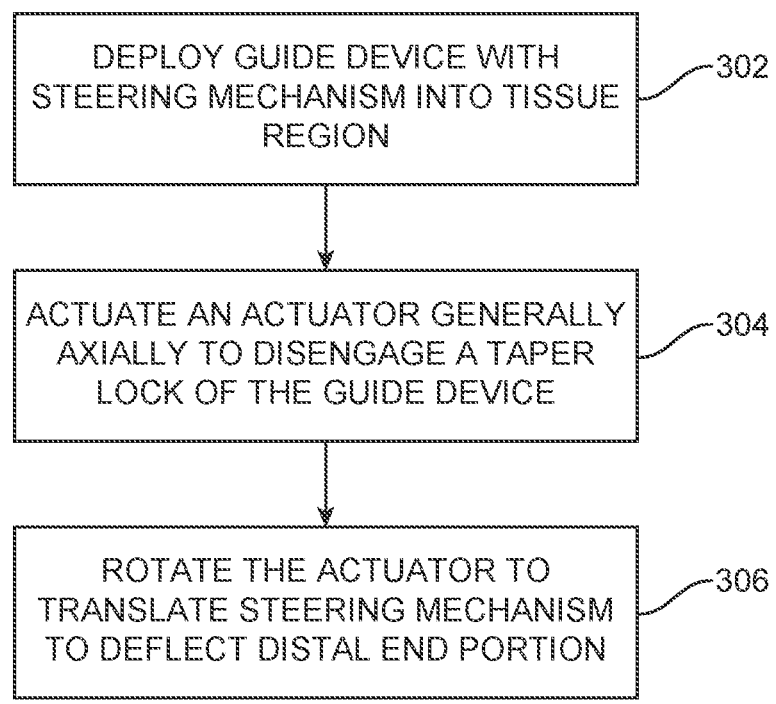
FIG. 10 depicts a method in accordance with an embodiment of this disclosure.

Turning to the embodiments of FIGS. 8-10, another exemplary steerable guide catheter is described. This exemplary steerable guide catheter provides a mechanical advantage sufficient to translate relatively small increments of clinician control into relatively larger increments of guide tube deflection with the use of a fast-pitch lead screw that is non-self-locking. Additionally, the steerable guide catheter provides a locking feature that is adapted to lock rotation of a steering assembly of the guide catheter such that the steerable guide catheter can be locked or otherwise maintained in a desired position (e.g., a position with the distal tip of the guide tube deflected toward a wall of a vessel).

FIG. 8 shows a handle 214 having a steering assembly 217 according to another embodiment of the present disclosure. Similar to the previously discussed embodiment, the handle 214 includes a proximal opening 222, a guide pathway 226, a hemostatic seal assembly (not shown) and a housing 236. The steering assembly 217 includes an actuator 218, a lead screw 219, and a slider 240 (illustrated in phantom). The actuator 218 includes a locking feature 250.

The handle 214 is coupled to a flexible guide tube 212 having a distal end portion (not shown) configured to deflect via actuation of a pull wire 220. The steering assembly 217 is configured to actuate the pull wire 220 to deflect the distal end portion of the guide tube 212 (such deflection is illustrated in FIG. 1). The actuator 218 is disposed at a distal end of the handle 214 and comprises a knob 251 that is coupled to the locking feature 250. The locking feature 250 extends proximally into an interior of the handle 214 and couples to the steering assembly 217. The actuator 218 is configured to rotate about a longitudinal axis of the guide catheter. As will be discussed subsequently, the actuator 218 is rotatable to drive translating movement of the slider 240. The locking feature 250 (e.g., a taper lock and spring element) is adapted to lock rotation of the actuator 218. The locking feature 250 allows the deflected position of the distal end portion of the flexible guide tube 212 to be maintained without the need for the clinician to keep a hand on the knob 251.

The lead screw 219 is coupled to the actuator 218 for rotation therewith. In particular, the lead screw 219 is coupled to a proximal end of the taper lock 258. The lead screw 219 can be configured to allow the guide pathway 226 to extend therethrough, thereby allowing for passage of additional operative tools (not shown) and the pull wire 220, which is coupled to the slider 240. According to one embodiment, the lead screw 219 can comprise a non-self-locking lead screw, and therefore, has a thread with an angle of greater than 5°. According to one embodiment, the lead screw 219 can have a lead of between 0.3 inch/revolution and 6.0 inches/revolution. According to another embodiment, the lead screw 219 can have a lead between 0.5 inch/revolution and 2.0 inches/revolution.

The slider 240 is coupled to the lead screw 219 and has the pull wire 220 attached thereto. According to the embodiment of FIG. 8, the slider 240 is adapted for translation (but not rotation) relative to the housing 236. The slider 240 and the lead screw 219 are coupled such that rotation of the lead screw 219 causes translation of the slider 240. During operation, the tension of the pull wire 220 generates a translational force on the slider 240 that is transferred through the lead screw 219 and is resolved by the handle 214. Thus, the handle 214 can be configured with one or more features (e.g., ribs 260) to resolve the translational force on the lead screw 219 due to the resultant force applied by the pull wire 220 on the slider 240.

In FIG. 8, the locking feature 250 comprises a biased element having a tapered outer surface 252 adapted to engage the one or more mating features 254 of the handle 214 to arrest rotation of the actuator 218. The one or more mating features 254 comprise surfaces of the handle 214 (rib portions of the housing 236) that are adapted to interface with and have a corresponding shape to that of the tapered outer surface 252. According to the provided embodiment, the locking feature 250 can comprise the taper feature (e.g. a taper lock 258) between the knob 251 and handle 214. To engage the lock, a spring 256, sometimes called a spring element 256, pushes the knob 251 distally and engages the locking feature between the two components. The friction between the two components can prevent rotation. To disengage the lock, the user can apply an axial force to the knob 251, to overcome the spring force of the spring 256, in the proximal direction to disengage the taper. More particularly, the locking feature 250 comprises the spring element 256 and the taper lock 258. The taper lock 258 is coupled between the knob 251 and the lead screw 219 (e.g., steering mechanism) and is biased to automatically lock rotation of the knob 251. The spring element 256 is configured to bias the taper lock 258 generally distally such that tapered outer surface 252 is forced against the features 254. The spring force applied by the spring element 256 can be between 0.5 lbf and 20 lbf in some instances. In yet further embodiments, the spring force applied by the spring element 256 can be between 2.0 lbf and 4.0 lbf. According to further embodiments, the tapered outer surface 252 can have an angle between 0.25° and 15°. In further embodiments, the tapered outer surface 252 can have an angle between 1.0° and 5°.

According to one embodiment, the actuator 218 can be configured to be actuated generally axially along the longitudinal axis in one of a proximal or distal direction (e.g., the knob 251 can be grasped and depressed axially or moved axially along the guide tube 212) to overcome the bias of the spring element 256 and to disengage the tapered outer surface 252 from the one or more mating features 254 of the handle 214 to allow for rotation of the actuator 218, translation of the slider 240, etc.

FIG. 9 shows the actuator 218 and the lead screw 219 according to one embodiment. The actuator 218 comprises the locking feature 250 and the knob 251. In the embodiment of FIG. 9, a coupling feature 270 is disposed between the actuator 218 and the lead screw 219. The coupling feature 270 can comprise a first coupling element 272 (e.g. a non-circular shaft such as a hexagonal head as illustrated) on the lead screw 219 and a second coupling element 274 on the actuator 218 (e.g., a hexagonally shaped socket). The first and second coupling elements 272, 274 are configured to decouple the translational force on the lead screw 219 that results from the tension on the pull wire 220 (FIG. 8) from being applied to the actuator 218. In particular, the depth in the axial direction of the hexagonal socket in FIG. 9 exceeds the axial extent of the hexagonal head. Thus, the actuator 218 and the lead screw 219 would not make contact in the axial direction. Therefore, the translational force on the lead screw 219 would be resolved against the handle 214 (FIG. 8), in particular, ribs 260 (FIG. 8) rather than the actuator 218. In this manner, the translational force on the lead screw 219 that results from tension of the pull wire 220 (FIG. 8) is decoupled from the actuator 218.

FIG. 10 illustrates a method according to an embodiment of the present disclosure. In an operation 302, the method deploys a guide device with an actuator and mechanism (steering mechanism) into an interior tissue region. The guide device can have a taper lock coupled between the actuator and the mechanism and can be adapted to lock rotation of the actuator. In an operation 304, the method can also actuate the actuator generally axially along a longitudinal axis about which the actuator is rotatable to disengage the taper lock from the one or more surfaces to allow for a translating movement of a component of the mechanism. In an operation 306, the method can rotate the actuator to produce the translating movement of the component (steering mechanism) to apply a force to deflect a distal end portion of the guide tube.

According to other embodiments, the method can be used in combination with passing an operative tool configured to apply one or more fasteners to tissue through the guide device. In further embodiments, the operative tool is operated while residing in the guide device to apply the one or more fasteners to tissue. The method can utilize a guide device that has a coupler configured to decouple a translational force on the mechanism from being applied to the actuator.

To further illustrate the implant and methods disclosed herein, a non-limiting list of embodiments is provided here:

In Example 1, an endovascular guide catheter can comprise a flexible guide tube and a handle. The flexible guide tube can have a distal end portion configured to deflect via actuation of a pull wire. The handle can be coupled to the guide tube and can comprise a steering assembly configured to actuate the pull wire to deflect the distal end portion of the guide tube. The steering assembly can comprise a stationary rack, a gear engaging the rack, a reel and a slider. The reel can be coupled to and configured to rotate with the gear. The pull wire can be coupled to the reel such that rotation of the reel causes the pull wire to wind or unwind around the reel. The slider can be adapted for translation relative to the rack. The translation of the slider can translate the reel relative to the rack and rotation of the gear along the rack can rotate the reel.

In Example 2, the guide catheter of Example 1, wherein the gear is coupled to the slider and translation of the slider translates and rotates the gear along the rack.

In Example 3, the guide catheter of Example 1, wherein the steering assembly can include an actuator disposed at a distal end of the handle, the actuator can be configured to rotate about a longitudinal axis of the guide catheter to drive the translation of the slider relative to the rack, wherein the actuator can be externally disposed about and can be coupled to a threaded rod, and wherein the threaded rod can be configured for translational movement and can be coupled to the slider assembly at a proximal end portion.

In Example 4, the guide catheter of Example 1, wherein the reel can be integral with the gear such that the reel is directly coupled without further intermediate components to the gear.

In Example 5, the guide catheter of Example 1, wherein the gear can be directly coupled via only a pin to the slider.

In Example 6, the guide catheter of Example 1, wherein the rack can comprise two rack portions and the gear can comprise two gear portions arranged between the reel, wherein each rack portion can be disposed generally parallel with the other to either side of the reel and one of the two gear portions can be adapted to engage one of the two rack portions.

In Example 7, the guide catheter of Example 1, wherein the slider assembly can be adapted to receive at least a portion of both the reel and the gear therein.

In Example 8, the guide catheter of Example 1, wherein the gear can be adapted to engage with the rack to translate movement of the slider assembly into rotation that rotates the reel.

In Example 9, the guide catheter of Example 1, wherein the gear and the rack can be adapted to be self-locking such that the reel cannot wind or unwind the pull wire without actuation by a user.

In Example 10, the guide catheter of Example 1, wherein a travel distance of the pull wire can comprise a combination of a linear travel of the slider and an amount of winding or unwinding due to rotation of the reel.

In Example 11, a system including the guide catheter of Example 1, can be in combination with an operative tool that is configured to apply one or more fasteners to tissue.

In Example 12, a steering assembly for and configured to be disposed within a handle of an endovascular guide catheter, the steering assembly can comprise a stationary rack, a gear engaging the rack, a reel, and a slider. The reel can be coupled to and configured to rotate with the gear. The pull wire can be coupled to the reel such that rotation of the reel causes the pull wire to wind or unwind around the reel. The slider can be adapted for translation relative to the rack. Translation of the slider can translate the reel relative to the rack and rotation of the gear along the rack can rotate the reel.

In Example 13, the assembly of Example 12, wherein the reel can be directly coupled without intermediate components to the gear and the gear can be directly coupled without intermediate components to the slider.

In Example 14, the assembly of Example 12, wherein the rack can comprise two rack portions and the gear can comprise two gear portions, wherein each rack portion can be disposed generally parallel with the other to either side of the reel and each one of the two gear portions can be adapted to engage one of the two rack portions.

In Example 15, the assembly of Example 12, can further comprise a pull wire configured to wind or unwind around the reel, wherein a travel distance of the pull wire can comprise a combination of a linear travel of the slider and an amount of winding or unwinding due to of rotation of the reel.

In Example 16, a system comprising the assembly of Example 12, and can further comprise an operative tool configured to apply one or more fasteners to tissue.

In Example 17, a guide device can comprising a flexible guide tube, a pull wire, a handle, and a reel. The flexible guide tube can have one or more lumens therein including a first lumen that defines a guide passage. The pull wire can extend along at least a portion of a length of the flexible guide tube and can be coupled to a distal end portion thereof, wherein the pull wire can be configured to apply a force to deflect the distal end portion. The handle can be coupled to the guide tube. The reel can be configured to rotate and translate relative to the handle to wind or unwind the pull wire about the reel to apply the force to deflect the distal end portion of the guide tube.

In Example 18, the guide device of Example 17, can further comprise a stationary rack disposed within the handle, a slider configured for translational movement relative to the rack, and a gear rotationally coupled to the slider assembly, wherein the reel can be integral with the gear such that the reel is directly coupled without further intermediate components to the gear.

In Example 19, a method can comprise deploying a guide device with a steering assembly comprising a rack, a reel, and a gear, into an interior tissue region, wherein the gear engages the rack and the reel coupled to the gear for rotation and translation relative to the rack, and operating the steering assembly to deflect a distal end portion of a guide tube coupled to the guide device, the operating including rotating the reel to wind or unwind a pull wire about the reel to apply a force to deflect the distal end portion, wherein the force additionally comprises a tension on the pull wire due to a linear travel of the reel.

In Example 20, the method of Example 19, can further comprise passing an operative tool configured to apply one or more fasteners to tissue through the guide device; and operating the operative tool while residing in the guide device to apply the one or more fasteners to tissue.

In Example 21, an endovascular guide catheter can comprise a flexible guide tube and a handle. The flexible guide tube can have a distal end portion configured to deflect via actuation of a pull wire. The handle can be coupled to the guide tube and can comprise a steering assembly configured to actuate the pull wire to deflect the distal end portion of the guide tube. The steering assembly can comprise an actuator configured to rotate about a longitudinal axis of the guide catheter, the actuator can have a locking feature adapted to lock rotation of the actuator, a non-self-locking lead screw coupled to the actuator for rotation therewith, and a slider coupled to the lead screw and having the pull wire attached thereto, the slider and lead screw being coupled such that rotation of the lead screw causes translation of the slider.

In Example 22, the guide catheter of Example 21, wherein the handle can be configured with one or more features to resolve a translational force on the lead screw due to a resultant force applied by the pull wire to the slider.

In Example 23, the guide catheter of Example 22, wherein one or more of the lead screw and actuator can include a coupling element that is configured to decouple the translational force on the lead screw from being applied to the actuator.

In Example 24, the guide catheter of Example 23, wherein the coupling element can comprise a hexagonal head, and wherein the hexagonal head can be received in a hexagonal shaped socket in one of the actuator or lead screw.

In Example 25, the guide catheter of Example 21, wherein the locking feature can comprise a biased element having a tapered outer surface adapted to engage the one or more mating features of the handle to arrest rotation of the actuator.

In Example 26, the guide catheter of Example 25, wherein the actuator can be configured to be actuated generally axially along the longitudinal axis in one of a proximal or distal direction to disengage the tapered outer surface from the one or more mating features of the handle to allow for rotation of the actuator, and wherein the actuator is rotatable to drive translating movement of the slider.

In Example 27, the guide catheter of Example 25, wherein the one or more mating features can comprise surfaces of the handle that are adapted to interface with and can have a corresponding shape to the tapered outer surface of the biased element.

In Example 28, the guide catheter of Example 25, wherein the tapered outer surface can have an angle between 0.25° and 15°.

In Example 29, the guide catheter of Example 25, wherein the actuator can comprise a knob disposed at a distal end portion of the handle and coupled to the locking feature, and wherein the locking feature extends proximally into an interior of the handle.

In Example 30, the guide catheter of Example 25, wherein the biased element can include a spring adapted to apply between 0.5 lbf to 20.0 lbf of force on the knob to engage the knob with the locking feature.

In Example 31, the guide catheter of Example 30, wherein the spring can be adapted to apply between 2.0 lbf to 4.0 lbf of force on the knob, and wherein the knob can be biased distally by the spring to engage the locking feature.

In Example 32, the guide catheter of Example 21, wherein at least a portion of the lead screw can be configured to allow the pull wire to extend therethrough.

In Example 33, a system including the guide catheter of Example 21, can be in combination with an operative tool that is configured to apply one or more fasteners to tissue.

In Example 34, the guide catheter of Example 21, wherein the lead screw can have a thread angle of greater than 5°.

In Example 35, the guide catheter of Example 21, wherein the lead screw can have a lead of between 0.5 inch/revolution and 2.0 inch/revolution.

In Example 36, a steering assembly for an endovascular guide device, the steering assembly can comprise a knob, a non-self-locking mechanism, and a taper lock. The knob can be configured for rotational movement about a longitudinal axis of the guide device. The non-self-locking mechanism can be disposed at least partially within the handle and can be coupled for rotation with the knob. The mechanism can be operable to transform rotational movement of the knob into translational movement of a component of the mechanism. The taper lock can be coupled between the knob and the mechanism and biased to automatically lock rotation of the knob. The knob can be configured to be actuated along the longitudinal axis to overcome the bias to disengage the taper lock to allow the rotational movement of the knob to cause translational movement of the component of the mechanism.

In Example 37, the assembly of Example 36, wherein the handle can include a housing configured with one or more features to resolve a translational force on the mechanism.

In Example 38, the assembly of Example 36, wherein one or more of the taper lock or the mechanism can include a coupler that is configured to decouple the translational force on the mechanism from being applied to the knob.

In Example 39, the assembly of Example 38, wherein the coupler can comprise a non-rounded shaft, and wherein the non-rounded shaft can be received in a correspondingly shaped recess in one of the taper lock or mechanism.

In Example 40, the assembly of Example 36, wherein the mechanism can include a non-self-locking lead screw having a lead screw angle of greater than 5°, and wherein the lead screw can be coupled through the taper lock to the knob for rotation therewith and the component can be coupled to the lead screw to translate relative thereto.

In Example 41, a system including the assembly of Example 36, can be in combination with the steering assembly and an operative tool configured to apply one or more fasteners to tissue.

In Example 42, a method can comprise deploying a guide device with an actuator and mechanism into an interior tissue region, the guide device having a taper lock coupled between the actuator and the mechanism and adapted to lock rotation of the actuator, actuating the actuator generally axially along a longitudinal axis about which the actuator is rotatable to disengage the taper lock from the one or more surfaces to allow for a translating movement of a component of the mechanism, and rotating the actuator to produce the translating movement of the component to apply a force to deflect a distal end portion of the guide tube.

In Example 43, the method of Example 42, can further comprise passing an operative tool configured to apply one or more fasteners to tissue through the guide device, and operating the operative tool while residing in the guide device to apply the one or more fasteners to tissue.

In Example 44, the method of Example 42, wherein the guide device can have a coupler configured to decouple a translational force on the mechanism from being applied to the actuator.

In Example 45, a guide device can comprise a flexible guide tube, a pull wire, a handle, a knob, and a steering mechanism. The flexible guide tube can have one or more lumens therein including a first lumen that defines a guide passage. The pull wire can extend along at least a portion of a length of the flexible guide tube and can be coupled to a distal end portion thereof. The pull wire can be configured to apply a force that deflects the distal end portion. The handle can be coupled to the guide tube. The knob can be configured to rotate about a longitudinal axis of the guide device, the knob can have a locking feature adapted to lock rotation of the knob. The steering mechanism can be disposed at least partially within the handle and coupled for rotation with the knob. The mechanism can be non-self-locking and can be operable to transform rotational movement of the knob into translational movement of a component of the mechanism to apply the force to the pull wire that deflects the distal end portion.

In Example 46, the device of Example 45, wherein the handle can include a housing configured with one or more features to resolve a translational force on the steering mechanism.

In Example 47, the device of Example 46, wherein one or more of the taper lock or the steering mechanism can include a coupler that is configured to decouple the translational force on the mechanism from being applied to the knob.

In Example 48, the device of Example 47, wherein the coupler can comprise a non-rounded shaft, and wherein the non-rounded shaft can be received in a correspondingly shaped recess in one of the taper lock or steering mechanism.

In Example 49, the device of Example 45, wherein the steering mechanism can include a non-self-locking lead screw that can have a lead screw angle of greater than 5°, and wherein the lead screw can be coupled through the taper lock to the knob for rotation therewith and the component can be coupled to the lead screw to translate relative thereto.

In Example 50, a system including the device of Example 45, can be in combination with the guide device and an operative tool configured to apply one or more fasteners to tissue.

In Example 51, the implant or method of any one or any combination of Examples 1-50 can optionally be configured such that all elements or options recited are available to use or select from.

These and other embodiments and features of the present implants and methods are set forth in part in the Detailed Description. The embodiments are intended to provide non-limiting examples of the present subject matter—it is not intended to provide an exclusive or exhaustive explanation. The Detailed Description is included to provide further information about the present apparatus, systems and methods.

Although specific configurations of steerable guide catheters are shown in FIGS. 1-10 and particularly described above, other designs of the steerable guide catheter and related operative tools that fall within the scope of the claims are anticipated. For example, the operative tool described herein comprises a fastener applier, however, other operative tools could be used with the steerable guide catheters. Indeed, operative tools adapted to deliver stents, grafts, graft-stents, balloons, wires, etc. can be used with the steerable guide catheters described herein.

The above detailed description includes references to the accompanying drawings, which form a part of the detailed description. The drawings show, by way of illustration, specific embodiments in which the inventive concept can be practiced. These embodiments are also referred to herein as "examples." Such embodiments can include elements in addition to those shown or described. However, other embodiments also contemplate examples in which only those elements shown or described are provided. Moreover, embodiments are contemplated using any combination or permutation of those elements shown or described (or one or more aspects thereof), either with respect to a particular embodiment (or one or more aspects thereof), or with respect to other embodiments (or one or more aspects thereof) shown or described herein.

In the event of inconsistent usages between this document and any documents so incorporated by reference, the usage in this document controls. In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described embodiments (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the inventive concept should be determined with reference to the appended claims, along with the full scope of equivalents to which such claims are entitled.

What is claimed is:

1. An endovascular guide catheter comprising:
   a flexible guide tube having a distal end portion configured to deflect via actuation of a pull wire; and
   a handle coupled to the guide tube and comprising a steering assembly configured to actuate the pull wire to deflect the distal end portion of the guide tube, the steering assembly comprising:
   an actuator configured to rotate about a longitudinal axis of the guide catheter, the actuator having a locking feature adapted to lock rotation of the actuator;
   a non-self-locking lead screw coupled to the actuator for rotation therewith; and
   a slider coupled to the lead screw and having the pull wire attached thereto, the slider and lead screw being coupled such that rotation of the lead screw causes translation of the slider, wherein the locking feature comprises a biased element having a tapered outer surface adapted to engage one or more mating features of the handle to arrest rotation of the actuator, wherein the actuator is configured to be actuated generally axially along the longitudinal axis in one of a proximal or distal direction to disengage the tapered outer surface from the one or more mating features of the handle to allow for rotation of the actuator, and wherein the actuator is rotatable to drive translating movement of the slider.

2. The guide catheter of claim 1, wherein the handle is configured with one or more features to resolve a translational force on the lead screw due to a resultant force applied by the pull wire to the slider.

3. The guide catheter of claim 1, wherein the one or more mating features comprise surfaces of the handle that are adapted to interface with and have a corresponding shape to the tapered outer surface of the biased element.

4. The guide catheter of claim 1, wherein the actuator comprises a knob disposed at a distal end portion of the handle and coupled to the locking feature, and wherein the locking feature extends proximally into an interior of the handle.

5. A system including the guide catheter of claim 1, in combination with an operative tool that is configured to apply one or more fasteners to tissue.

6. The guide catheter of claim 2, wherein one or more of the lead screw and actuator includes a coupling element that is configured to decouple the translational force on the lead screw from being applied to the actuator.

7. The guide catheter of claim 4, wherein the biased element includes a spring adapted to apply force on the knob to engage the knob with the locking feature.

* * * * *